US012727794B2

(12) United States Patent
Chang et al.

(10) Patent No.: US 12,727,794 B2
(45) Date of Patent: Sep. 8, 2026

(54) WEARABLE DEVICE AND A METHOD FOR SELECTING AND INTERPRETING LIGHT INTENSITY DATA VALUES APPLICABLE THERETO

(71) Applicants: NATIONAL TAIPEI UNIVERSITY OF TECHNOLOGY, Taipei City (TW); TAIPEI MEDICAL UNIVERSITY, Taipei City (TW)

(72) Inventors: Cheng-Chun Chang, Taipei City (TW); Po-Wen Lu, Taipei City (TW)

(73) Assignees: NATIONAL TAIPEI UNIVERSITY OF TECHNOLOGY, Taipei City (TW); TAIPEI MEDICAL UNIVERSITY, Taipei City (TW)

( * ) Notice: Subject to any disclaimer, the term of this patent is extended or adjusted under 35 U.S.C. 154(b) by 361 days.

(21) Appl. No.: 18/400,268

(22) Filed: Dec. 29, 2023

(65) Prior Publication Data

US 2024/0215875 A1 Jul. 4, 2024

(30) Foreign Application Priority Data

Dec. 30, 2022 (TW) ................................ 111150853

(51) Int. Cl.
*A61B 5/00* (2006.01)
*A61B 5/1455* (2006.01)

(52) U.S. Cl.
CPC ............ *A61B 5/1455* (2013.01); *A61B 5/681* (2013.01); *A61B 5/7203* (2013.01);
(Continued)

(58) Field of Classification Search
CPC ..... A61B 5/1455; A61B 5/681; A61B 5/7203; A61B 5/7267; A61B 2560/0443;
(Continued)

(56) References Cited

U.S. PATENT DOCUMENTS 10,568,525 B1 * 2/2020 Wu ...................... A61B 5/6824
10,765,331 B2 * 9/2020 Morris .................. A61B 5/024
(Continued)

OTHER PUBLICATIONS

Y. Kurylyak, F. Lamonaca and D. Grimaldi, "A Neural Network-based method for continuous blood pressure estimation from a PPG signal". in proc. of 2013 IEEE I2MTC, Minneapolis, MN, pp. 280-283, 2013.

*Primary Examiner* — May A Abouelela
(74) *Attorney, Agent, or Firm* — WPAT, PC

(57) ABSTRACT

A wearable device and a method for selecting and interpreting light intensity data values applicable thereto. The wearable device includes a light emitting unit and a spectrum sensing unit. The method includes steps of: controlling the light-emitting unit to simultaneously emit a mixed light including multiple spectrum frequency bands to enter inside skin of the user; controlling the spectrum sensing unit to sense the intensity of an outgoing light from inside skin of the user at a series of sampling time to generate a spectrum data set including a plurality of groups of frequency band-light intensity data values; and selecting at least one of a first group of frequency band-light intensity data values satisfying a signal quality index in the spectrum data set to perform a data interpretation at a first judgment time point.

13 Claims, 7 Drawing Sheets

(52) U.S. Cl.
CPC .... *A61B 5/7267* (2013.01); *A61B 2560/0443* (2013.01); *A61B 2562/0238* (2013.01); *A61B 2562/0242* (2013.01)

(58) Field of Classification Search
CPC .... A61B 2562/0238; A61B 2562/0242; A61B 5/02416; A61B 5/14532; A61B 5/00
See application file for complete search history.

(56) References Cited

U.S. PATENT DOCUMENTS 11,540,752 B1 * 1/2023 Miller .................... A61B 5/681
11,589,815 B1 * 2/2023 Williams ............. A61B 5/7405
11,771,350 B1 * 10/2023 Mannheimer ...... A61B 5/14552 600/323
11,848,102 B2 * 12/2023 Matichuk ......... G06K 19/07762
11,850,071 B1 * 12/2023 Coakley ................. A61B 5/332
11,986,644 B2 * 5/2024 Tal ...................... A61M 60/178
12,070,333 B2 * 8/2024 Bremer .............. A61B 5/14552
12,396,686 B2 * 8/2025 Tadele ................... A61B 5/681
12,467,933 B2 * 11/2025 Forzani ................ G01N 33/726
2008/0208009 A1 * 8/2008 Shklarski ............... G16H 40/67 600/324
2013/0296674 A1 * 11/2013 Watson ................ A61B 5/1495 600/324
2014/0275852 A1 * 9/2014 Hong ................... A61B 5/0002 600/479
2014/0288435 A1 * 9/2014 Richards .............. A61B 5/1123 600/479
2014/0378777 A1 * 12/2014 Conrad .................. G16H 40/63 600/301
2015/0173631 A1 * 6/2015 Richards .............. A61B 5/7282 600/479
2015/0265217 A1 * 9/2015 Penders ................... A61B 5/33 600/300
2016/0029967 A1 * 2/2016 Lee .................... A61B 5/02438 600/479
2016/0058310 A1 * 3/2016 Iijima .................... A61B 5/681 600/476
2016/0199000 A1 * 7/2016 Gimenez ............... G01J 1/4204 250/208.6
2017/0209049 A1 * 7/2017 Wang ................... A61B 5/0071
2017/0209055 A1 * 7/2017 Pantelopoulos ..... A61B 5/7203
2018/0035943 A1 * 2/2018 Shemesh .............. A61B 5/0205
2018/0070839 A1 * 3/2018 Ritscher ............... A61B 5/4815
2018/0085058 A1 * 3/2018 Chakravarthi ......... G16H 40/67
2018/0156660 A1 * 6/2018 Turgeon .................... G01J 1/44
2018/0214088 A1 * 8/2018 Newberry ............ A61B 5/6817
2018/0333053 A1 * 11/2018 Verkruijsse .......... A61B 5/0295
2018/0360373 A1 * 12/2018 Aarts ................ A61B 5/14507
2019/0015014 A1 * 1/2019 Lange .................. A61B 5/1455
2019/0159690 A1 * 5/2019 Patel ................. A61B 5/02438
2019/0286233 A1 * 9/2019 Newberry ............ A61B 5/1121
2019/0380586 A1 * 12/2019 Park ..................... A61B 5/0059
2020/0138379 A1 * 5/2020 Huiku .................. A61B 5/7221
2020/0237317 A1 * 7/2020 Newberry ............ A61B 5/1455
2020/0375513 A1 * 12/2020 Kasbekar ............. A61B 5/6826
2021/0059586 A1 * 3/2021 Marriott ............... A61B 5/7225
2021/0321917 A1 * 10/2021 Choi .................... A61B 5/6801
2021/0337885 A1 * 11/2021 Connor ................ A41C 3/0064
2021/0345949 A1 * 11/2021 Edouard ................ A61B 5/681
2021/0353168 A1 * 11/2021 Olivier ............... A61B 5/02416
2022/0133241 A1 * 5/2022 Jones ................... A61B 5/1032 600/485
2022/0142569 A1 * 5/2022 Tsai ....................... G04G 17/08
2022/0175261 A1 * 6/2022 Li ........................ A61B 5/6826
2022/0249021 A1 * 8/2022 Ahmad ................ A61B 5/0205
2022/0265214 A1 * 8/2022 Jariwala ................. A61B 5/296
2022/0313098 A1 * 10/2022 LeBoeuf .............. A61B 5/7221
2023/0045200 A1 * 2/2023 Shan .................. A61B 5/02416
2023/0114269 A1 * 4/2023 Heikkinen ........... A61B 5/6826 600/323
2023/0168761 A1 * 6/2023 Park ....................... G04G 21/08 345/174
2023/0210390 A1 * 7/2023 Ben Ishay ............ A61B 5/1455 356/337
2023/0335271 A1 * 10/2023 Dastmalchi .......... A61B 5/7264
2024/0008812 A1 * 1/2024 Benson .............. A61B 5/14546
2024/0041332 A1 * 2/2024 Lokare ................... A61B 5/725
2024/0115204 A1 * 4/2024 Xu ....................... A61B 5/0075
2024/0130687 A1 * 4/2024 Xu ....................... A61B 5/0075
2024/0179865 A1 * 5/2024 Tan ...................... H05K 7/1427
2025/0000399 A1 * 1/2025 Kernasovskiy ...... A61B 5/7203
2025/0072771 A1 * 3/2025 Cai ...................... A61B 5/0205

* cited by examiner

WEARABLE DEVICE AND A METHOD FOR SELECTING AND INTERPRETING LIGHT INTENSITY DATA VALUES APPLICABLE THERETO

BACKGROUND OF THE INVENTION

1. Field of the Invention

The present application relates to a wearable device and a method for selecting and interpreting light intensity data values applicable thereto, and especially to a wearable device applicable to a user' body and a method for selecting and interpreting light intensity data values applicable thereto.

2. The Prior Arts

With increasing popularity of wearables devices, many people wear smart watches or smart bracelets. Most of these wearable devices already have functions of monitoring physiological values for measuring and recording various data that can represent changes in the user's physical status, thereby monitoring the user's health status in real time.

Please refer to FIG. 1, which is a functional block diagram illustrating a conventional wearable device contacting the user's skin, wherein a bottom of the wearable device 11 contacts a surface of the user's skin 10. A photoplethysmography (hereafter PPG) module is usually set on the bottom of a main body 11 of the wearable device. In the conventional technical means, a traditional PPG module 110 only emits a light of single frequency band into inside skin at single time point, then detects an intensity change of outgoing light from the inside skin, thereby estimates a status of blood vessels in dermis and subcutaneous tissue, and finally estimates physiological status such as heart rate, pulse or blood pressure.

For example, when a light beam of certain wavelength irradiates on the skin surface, vasoconstriction and vasodilatation caused by each heartbeat will affect transmission of the light (such as to perform transmissive PPG to the light passing through fingertips) or reflection of the light (such as to perform reflective PPG to the light reflected from near wrist surface). When the light irradiates the skin tissue then is reflected to a light sensor, the intensity of the light will attenuate to a certain extent. When there is no large-scale movement of the measuring site, the light absorption of muscles, bones, veins and other connective tissue is basically unchanged, but arteries are different, there is obvious blood flow in arteries, the light absorption of that has significant change naturally. When the light is converted to electrical signals through PPG method, the signals obtained can be divided into DC signals and AC signals, precisely because the light absorption of arteries changes and that of the other tissues basically remain. Therefore, as long as the AC signals are extracted, characteristics of the blood flow can be reflected.

However, the light sensor for receiving the outgoing light in the traditional PPG module 110 can only convert the received outgoing light of single frequency band into a single signal curve in energy intensity change. Moreover, a displacement that is easily occurred between the wearable device and the skin causes change of an incident distance, so the measuring result is easily distorted due to the user's shaking. Furthermore, because sensing information that can be generated by the outgoing light of the single frequency band is not rich enough, the aforesaid deficiencies will eventually lead to misjudgments in the wearable device, which will make it impossible to monitor the user's health status in real time and effectively.

SUMMARY OF THE INVENTION

How to solve the aforesaid deficiencies in the traditional photoplethysmography module is the main purpose of developing technical means of the present application. The present invention main relates to a wearable device, which includes: a main body, including a casing, which includes a sensing surface that can be close to outside skin of the user; a physiological data sensing module, disposed in the casing, including a light emitting unit and a spectrum sensing unit, wherein the light emitting unit is used to simultaneously emit a mixed light including multiple spectrum frequency bands, and the mixed light enters inside skin of the user through the sensing surface; the spectrum sensing unit is used to sense an intensity of an outgoing light from inside skin of the user at a series of sampling time to generate a spectrum data set, the spectrum data set includes a plurality of light intensity data values, the plurality of light intensity data values can be divided into a plurality of groups of frequency band-light intensity data values respectively obtained corresponding to the plurality of spectrum frequency bands, and can be respectively divided into a plurality of sampling time-light intensity data value sets corresponding to the series of sampling time; and an arithmetic unit, with signal connecting to the physiological data sensing module, for receiving the spectrum data set; according to a signal quality of the plurality of groups of frequency band-light intensity data in the spectrum data set, the arithmetic unit selects at least one of a first group of frequency band-light intensity data values satisfying a signal quality index in the spectrum data set to perform a data interpretation at a first judgment time point, and selects at least one of a second group of frequency band-light intensity data values satisfying the signal quality index in the spectrum data set to perform the data interpretation at a second judgment time point.

According to the above concept, in the wearable device recited in the present application, the sensing surface is against outside wrist skin of the user, the physiological data sensing module is a micro spectrometer, the light emitting unit in the micro spectrometer includes light emitting diodes that is used to simultaneously emit the mixed light including multiple spectrum frequency bands, the spectrum sensing unit in the micro spectrometer is used to sense the outgoing light from inside skin of the user at the series of sampling time to generate a plurality of spectrum frequency bands-intensity signal curves, any one of the spectrum frequency bands-intensity signal curves is generated from one group of the frequency band-light intensity data values in the spectrum data set.

According to the above concept, in the wearable device recited in the present application, the arithmetic unit is disposed in the casing, signal connecting to the physiological data sensing module, for receiving the spectrum data set; according to a signal quality of the plurality of spectrum frequency band-intensity signal curves generated from the spectrum data set, the arithmetic unit selects one or more of the spectrum frequency band-intensity signal curves of the signal quality meeting a condition in the spectrum data set to perform the data interpretation at the first judgment time point, and additionally selects one or more of frequency band-intensity signal curves of the signal quality meeting the condition in the spectrum data set to perform the data interpretation at the second judgment time point; the signal quality the plurality of spectrum frequency band-intensity signal curves is its signal-to-noise ratio value.

According to the above concept, in the wearable device recited in the present application, in any one of the plurality of spectrum frequency band-intensity signal curves, signal components within a frequency band range from a lower limit frequency to an upper limit frequency are defined as the signal, and signal components outside the frequency band range from the lower limit frequency to the upper limit frequency are defined as the noise; the arithmetic unit respectively calculates a ratio of signal intensity and noise intensity of each the spectrum frequency band-intensity signal curve of the plurality of spectrum frequency band-intensity signal curves to obtain the signal-to-noise ratio value, then selects and determines one or more of the spectrum frequency band-intensity signal curves of the signal-to-noise ratio value greater than a preset value as a qualified spectrum frequency band-intensity signal curve, and performs a PPG data interpretation to one or more of the qualified spectrum frequency band-intensity signal curves.

According to the above concept, in the wearable device recited in the present application, the lower limit frequency is 0.5 Hz, the upper limit frequency limit is 7 Hz, the arithmetic unit performs a maximum ratio combining of the plurality of frequency band-intensity signal curves which meet a signal-to-noise ratio standard for weighting and combining them into an optimized intensity signal curve, and then uses the optimized intensity signal curve to perform the PPG data interpretation subsequently.

According to the above concept, in the wearable device recited in the present application, the PPG data interpretation can estimate one value of white blood cell count, red blood cell count, hemoglobin, hematocrit, blood glucose, blood pressure, blood urea nitrogen, creatinine and alanine aminotransferase (ALT) of the user.

According to the above concept, in the wearable device recited in the present application, the PPG data interpretation is optimized by using artificial intelligence learning, and simultaneously generates p spectrum frequency band-intensity signal curves corresponding p spectrum frequency bands to provide more data in a short time for training of an artificial intelligence program, which can quickly improve accuracy of the data interpretation.

According to the above concept, in the wearable device recited in the present application, the arithmetic unit determines whether measuring environment or device wearing conditions are correct according to a sampling time-light intensity data value sets corresponding to the plurality of spectrum frequency bands obtained at the same sampling time point.

According to the above concept, in the wearable device recited in the present application, the arithmetic unit determines measuring object characteristics according to a sampling time-light intensity data value sets corresponding to the plurality of spectrum frequency bands obtained at the same sampling time point, and selects an appropriate artificial intelligence model and prediction model according to the measuring object characteristics.

According to the above concept, in the wearable device recited in the present application, the arithmetic unit determines measuring object characteristics according to a sampling time-light intensity data value sets corresponding to the plurality of spectrum frequency bands obtained at the sampling time point, and selects a measuring parameter according to the measuring object characteristics, the measuring parameter is a light source intensity of an individual frequency band, a sampling speed and measuring times of the spectrum sensing unit, a lens aperture value or exposure value.

According to the above concept, in the wearable device recited in the present application, the arithmetic unit converts the spectrum data set into a flat color image, two-dimensional coordinates of the flat color image are the sampling time and the spectrum frequency band respectively, a color value of any coordinate point in the flat color image is a light intensity value, and the arithmetic unit perform the data interpretation to the flat color image by using a image recognition technology of convolutional neural network.

Another aspect of the present application is a wearable device, applicable to a user, including: a main body, including a casing, which includes a sensing surface that can be close to outside skin of the user; a physiological data sensing module, disposed in the casing, including a light emitting unit and a spectrum sensing unit, wherein the light emitting unit is used to emit an incident light of intensity changing with time, the incident light of different intensities enters inside skin of the user to different depths through the sensing surface; the spectrum sensing unit is used to sense an intensity of an outgoing light from inside skin of the user at a series of sampling time to generate a spectrum data set, the spectrum data set includes a plurality of light intensity data values, the plurality of light intensity data values can be divided into a plurality of groups of depth-light intensity data values respectively obtained corresponding to the plurality of incident light intensities; and an arithmetic unit, with signal connecting to the physiological data sensing module, for receiving the spectrum data set; according to a signal quality of the plurality of groups of depth-light intensity data in the spectrum data set, the arithmetic unit selects at least one of a first group of depth-light intensity data values satisfying a signal quality index in the spectrum data set to perform a data interpretation at a first judgment time point, and selects at least one of a second group of depth-light intensity data values satisfying the signal quality index in the spectrum data set to perform the data interpretation at a second judgment time point.

A further aspect of the present application is a method for selecting and interpreting light intensity data values, applicable between a user and a wearable device, the wearable device includes a light emitting unit and a spectrum sensing unit, the method includes following steps of: controlling the light emitting unit simultaneously emit a mixed light including multiple spectrum frequency bands, and the mixed light enter inside skin of the user through a sensing surface; controlling the spectrum sensing unit sense an intensity of an outgoing light from inside skin of the user at a series of sampling time to generate a spectrum data set, wherein the spectrum data set includes a plurality of light intensity data values, the plurality of light intensity data values can be divided into a plurality of groups of frequency band-light intensity data values respectively obtained corresponding to the plurality of spectrum frequency bands, and can be respectively divided into a plurality of sampling time-light intensity data value sets corresponding to the series of sampling time; and according to a signal quality of the plurality of groups of frequency band-light intensity data in the spectrum data set, selecting at least one of a first group of frequency band-light intensity data values satisfying a signal quality index in the spectrum data set to perform a data interpretation at a first judgment time point, and selecting at least one of a second group of frequency band-light intensity data values satisfying the signal quality index in the spectrum data set to perform the data interpretation at a second judgment time point.

Another aspect of the present application is a method for selecting and interpreting light intensity data values, applicable between a user and a wearable device, the wearable device includes a light emitting unit and a spectrum sensing unit, the method includes following steps of: controlling the light emitting unit emit, and incident light of intensity changing with time, wherein the incident light of different intensities enters inside skin of the user to different depths through the sensing surface; controlling the spectrum sensing unit sense an intensity of an outgoing light from inside skin of the user at a series of sampling time to generate a spectrum data set, wherein the spectrum data set includes a plurality of light intensity data values, the plurality of light intensity data values can be divided into a plurality of groups of depth-light intensity data values respectively obtained corresponding to the plurality of incident light intensities; and according to a signal quality of the plurality of groups of depth-light intensity data in the spectrum data set, selecting at least one of a first group of depth-light intensity data values satisfying a signal quality index in the spectrum data set to perform a data interpretation at a first judgment time point, and selecting at least one of a second group of depth-light intensity data values satisfying the signal quality index in the spectrum data set to perform the data interpretation at a second judgment time point.

In order to have a more clear understanding of the aforesaid concepts of the present invention, embodiments are provided below and described in detail accompanying with corresponding drawings.

DETAILED DESCRIPTION OF THE PREFERRED EMBODIMENT

Figure 1:
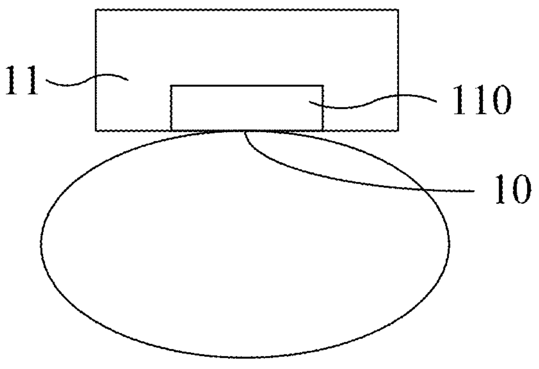
FIG. 1 is a functional block diagram illustrating a conventional wearable device contacting the user's skin.
Figure 2A:
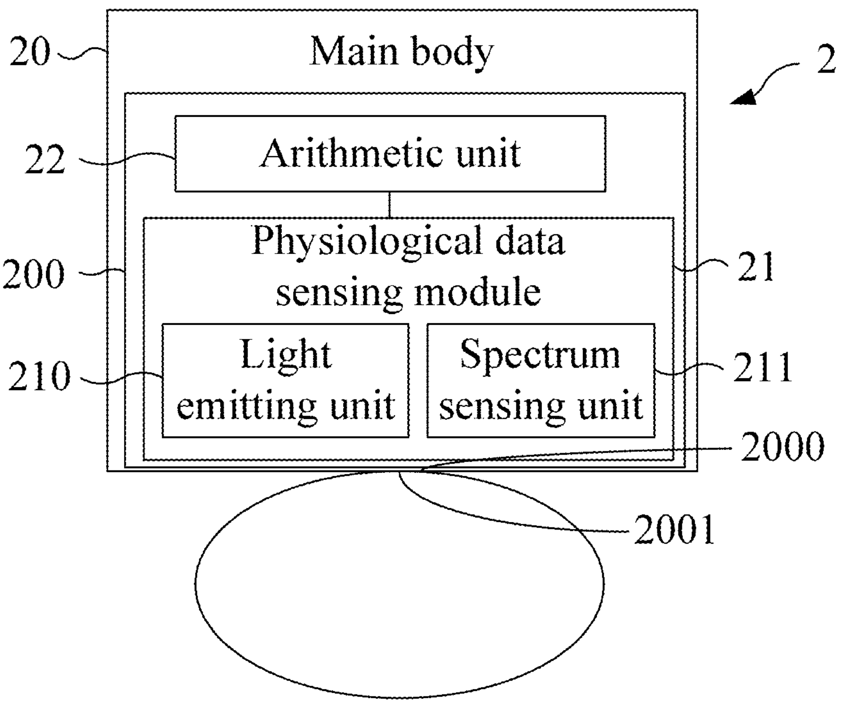
FIG. 2*a* is a functional block schematic diagram illustrating a wearable device developed by the present application.

For resolve the aforesaid problems, the inventor of the present application develops a wearable device having functional blocks as shown in FIG. 2*a*, which can be applicable to physiological data sensing. The wearable device mainly includes a main body 20, a physiological data sensing module 21 and an arithmetic unit 22, wherein the main body 20 includes a casing 200, the casing 200 includes a sensing surface 2000, and the sensing surface 2000 can be close to or even against skin surface of the user 2001.

Figure 2B:
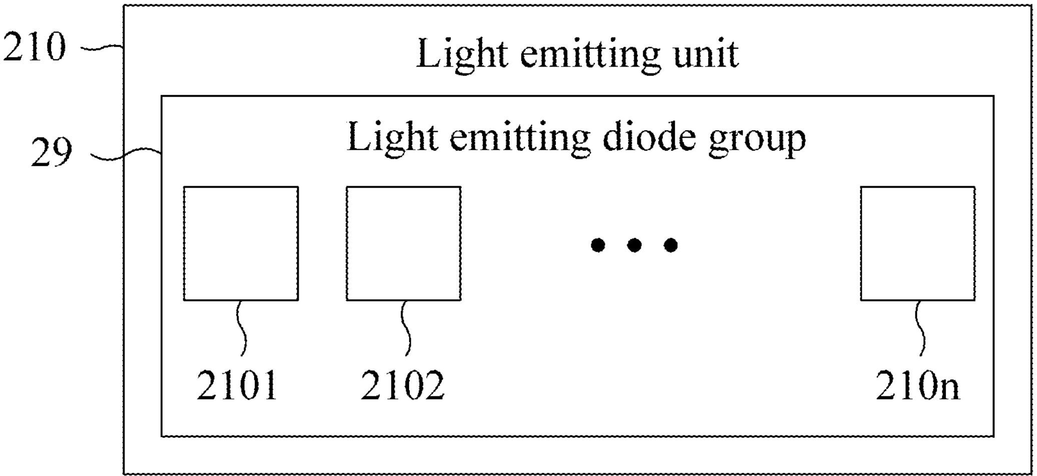
FIG. 2*b* is a functional block schematic diagram illustrating a light emitting unit developed by the present application.
Figure 2C:
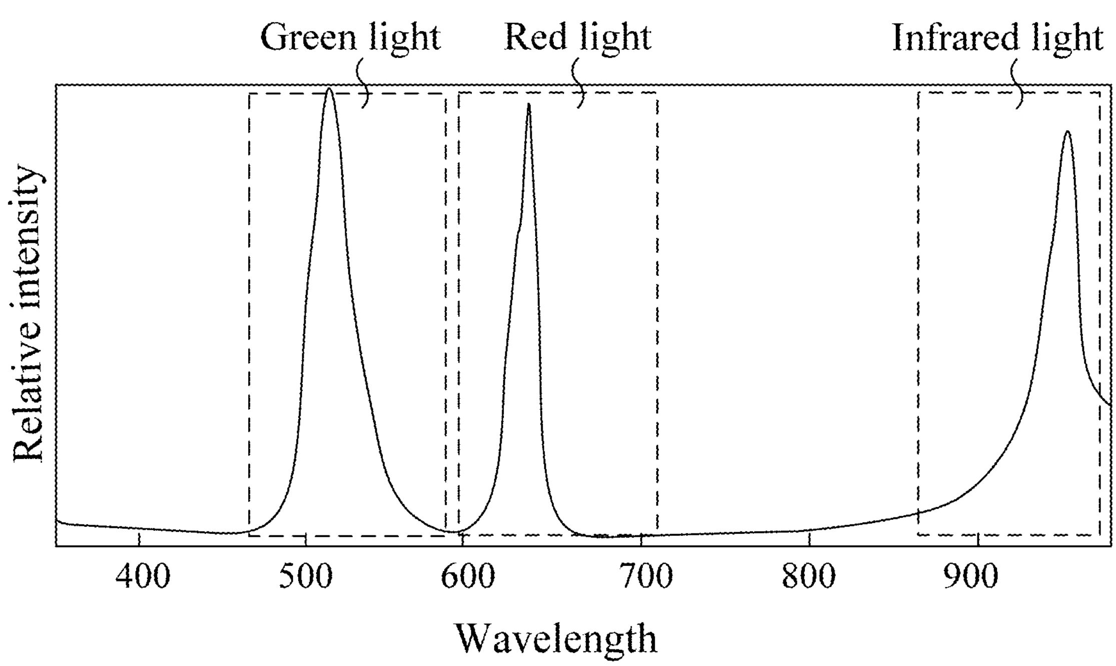
FIG. 2*c* is a spectrogram of the three light sources.

As for the physiological data sensing module 21, it can be disposed in the casing 200, and includes a light emitting unit 210 and a spectrum sensing unit 211, the light emitting unit 210 is mainly used to simultaneously emit a mixed light including multiple spectrum frequency bands. For example, the light emitting unit 210 can be equipped with a single light emitting diode of a frequency band capable of covering multiple-bands spectra (such as infrared, visible light and ultraviolet); or as a functional block schematic diagram illustrating a light emitting unit shown in FIG. 2*b*, the light emitting unit 210 can include a light emitting diode group 29 composed of plural light emitting diodes 2101, 2102 . . . 210*n* with different frequency bands. For example, the plural light emitting diodes can be the light emitting diodes with green light (wavelength 515 nm), red light (wavelength 660 nm) and infrared light (wavelength 940 nm) respectively, a spectrogram of the three light sources as shown in FIG. 2*c*.

Figure 2D:
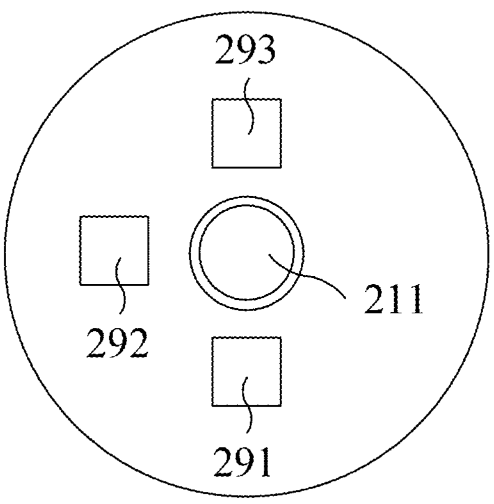
FIG. 2*d* is a schematic diagram illustrating elements configuration of the physiological data sensing module developed by the present application.

The mixed light of multiple spectrum frequency bands simultaneously emitted by the light emitting unit 210 enters the skin surface of the user 2001 through the sensing surface 2000. Since the incident light of different frequency bands can enter inside skin of the user to different depths, an outgoing light intensity change of different frequency bands (wavelength range) included in an outgoing mixed light from inside the skin surface of the user will carry the physiological status changes representing that occur at different depths. In order to receive light intensity signals in all frequency bands, the spectrum sensing unit 211 can be a Multi-Wavelength Photoplethysmography (hereafter MW-PPG) sensor, it can be completed with, for example, a micro spectrometer developed by nanoLambda company. As shown in FIG. 2*d*, the light emitting diode group 29 composed of the light emitting diodes 291, 292, 293 of green light (wavelength 515 nm), red light (wavelength 660 nm) and infrared light (wavelength 940 nm) can be disposed in the physiological data sensing module 21 developed by the present application, the light sources are arranged symmetrically; and the spectrum sensing unit 211 is placed in the middle, so that the outgoing light of different wavelengths from the inside skin can be gathered at center point to facilitate collection by the MW-PPG sensor. Compared with an area of the traditional spectrometer easily being several square centimeters, an area of this sensor only accounts for a few square millimeters, its structure does not require to use precision optical components such as grating, focal lenses; it is small and lightweight in use, and it can simultaneously collects the PPG signals of 153 wavelengths including 340 nm, 345 nm . . . 505 nm, 510 nm, 515 nm, 520 nm, 525 nm, 620 nm, 625 nm, 630 nm, 635 nm, 640 nm, 930 nm, 935 nm, 940 nm, 945 nm, 950 nm.

Figure 3A:
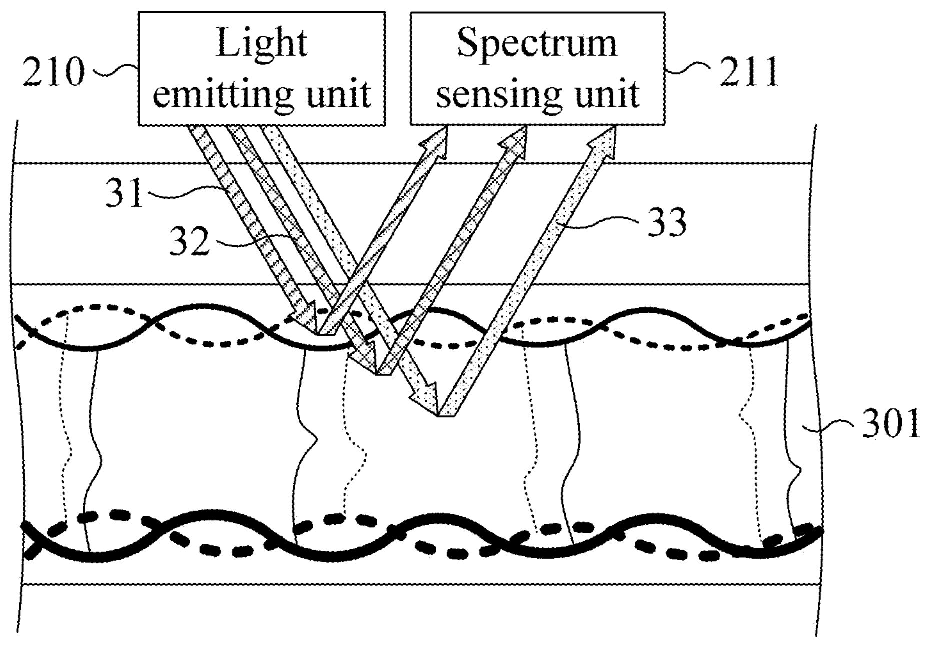
FIG. 3*a* is a schematic diagram illustrating incident light emitted by the wearable device of the present application.
Figure 3B:
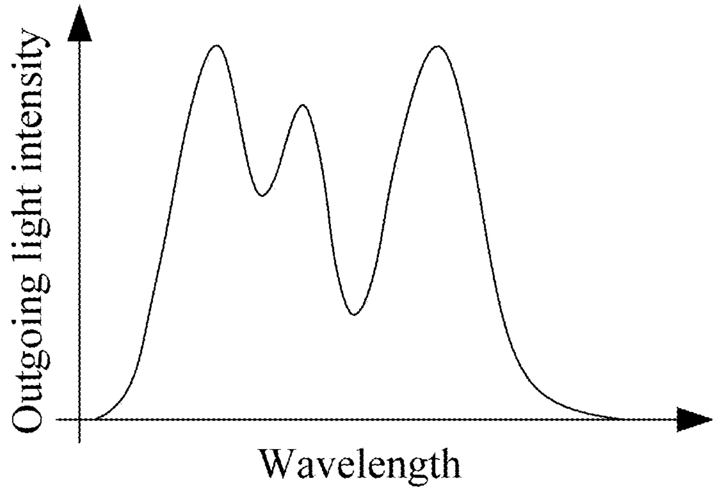
FIG. 3*b* is a diagram illustrating a representative example of outgoing light intensity distribution of three different frequency bands.

To take a schematic diagram of the incident light shown in FIG. 3*a* as an example, the incident light 31, 32, 33 of three different frequency bands (wavelength range) can enter different depths of dermis 301 in the user's skin, an outgoing light intensity distribution of the outgoing mixed light from inside the skin surface of the user at a certain sampling time point is as shown in FIG. 3*b*, in which the three peaks represent the main wavelength position of the incident light 31, 32, 33 of three different frequency bands (wavelength range). Since the incident light emitted by the light emitting unit 210 is the mixed light includes multiple frequency bands (infrared rays and visible light) at the same time, the outgoing light is also belong to the mixed light of multiple frequency bands. Therefore, the spectrum sensing unit 211 of the present application can be used to sense the outgoing mixed light of multiple-bands spectra from inside the skin surface of the user at a series of sampling time points T1, T2, . . . , Tn, and to generate a spectrum data set, the spectrum set includes n sampling time-light intensity data value sets corresponding to the series of sampling time points T1, T2, . . . , Tn.

For example, the first sampling time-light intensity data value group in the n sampling time-light intensity data value groups is composed of p light intensity data values corresponding to p spectrum frequency bands ($F_1$, $F_2$, . . . ,$F_p$) respectively obtained at the first sampling time point $T_1$. As for the second sampling time-light intensity data group in the n sampling time-light intensity data value groups, it is composed of p light intensity data values corresponding to p spectrum frequency bands ($F_1$, $F_2$, . . . ,$F_p$) respectively obtained at the second sampling time point $T_2$. According to a signal quality of the plurality of groups of frequency band-light intensity data in the spectrum data set, the arithmetic unit 22 can select at least one of the first group of frequency band-light intensity data values satisfying a signal quality index in the spectrum data set to perform data interpretation at a first judgment time point, and can also select at least one of the second group of frequency band-light intensity data values satisfying the signal quality index in the spectrum data set to perform the data interpretation at a second judgment time point. In this way, even if the relative displacement occurred between the wearable device and the user due to weak wearing causes variation in arrival depth of the incident light, at least a group of frequency band-light intensity data values measured with the best depth at that time can be instantly select to perform the data interpretation according to the signal quality, so that the misjudgments caused by depth variations can be avoided; or at least a group of frequency band-light intensity data values with the best measuring effect at that time can be instantly select to perform the data interpretation according to the signal quality, so that the misjudgments caused by measuring environmental changes, physiological changes or depth variations can be avoided.

Figure 3C:
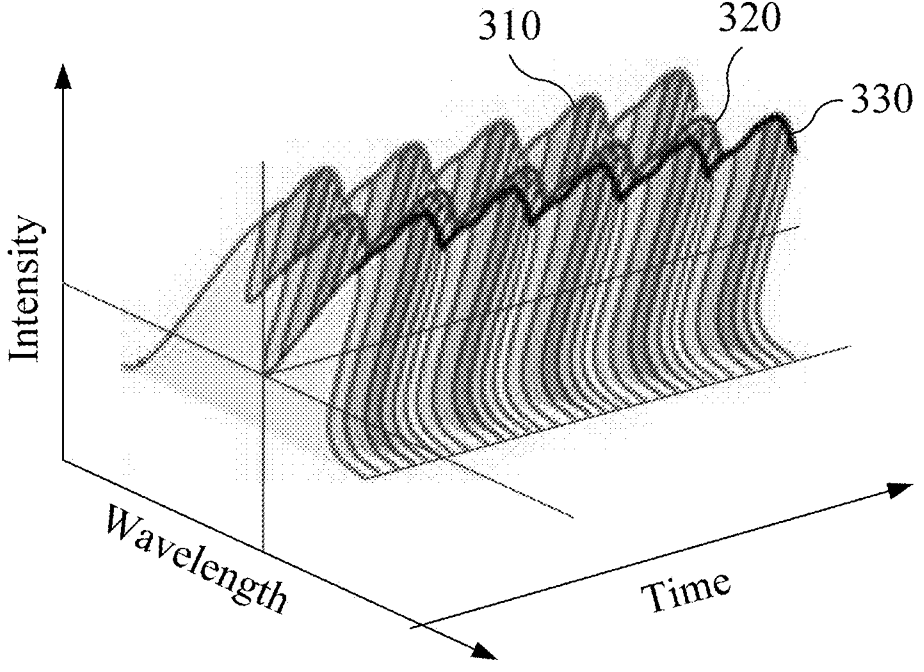
FIG. 3*c* is a schematic diagram illustrating three spectrum frequency band-intensity signal curves that change with time and correspond to different spectrum bands generated by the device of the present application.
Figure 4:
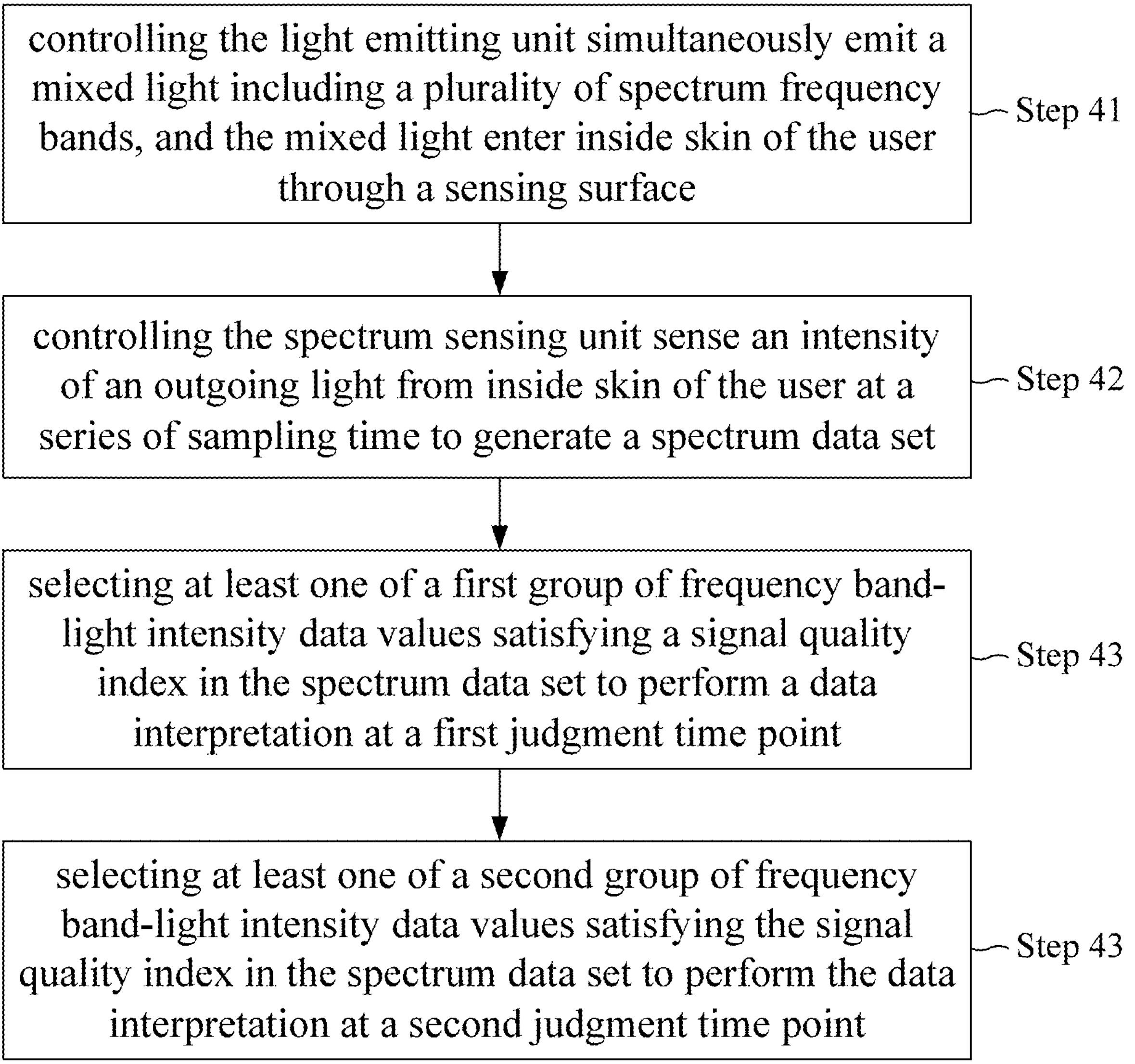
FIG. 4 is a flow chart illustrating a preferred embodiment of a method for selecting and interpreting light intensity data values developed by the present application.

In other words, p spectrum frequency band-intensity signal curves corresponding to the p spectrum frequency bands ($F_1$, $F_2$, . . . , $F_p$) can be generated according to the spectrum data set. To take the above FIG. 3*a* and FIG. 3*b* as examples, after the series of sampling time, three spectrum frequency band-intensity signal curves 310, 320, 330 as shown in FIG. 3*c* that vary over the time and correspond to different spectrum frequency bands can be obtained. From the above description and FIGS. 3*a*-3*c*, it can be seen that the spectrum data set obtained by utilizing the hardware setting of the present application can generates the p spectrum frequency band-intensity signal curves representing different skin depths; in this way, the arithmetic unit 22 with signal connecting to the physiological data sensing module 21 (the arithmetic unit 22 can be disposed in the casing 200 or in a cloud) can receive the spectrum data generated by the aforesaid spectrum sensing unit 211. In this way, according to the signal quality of the plurality of p groups of frequency band-light intensity data in the spectrum data set, the arithmetic unit 22 can select at least one of the first group of frequency band-light intensity data values satisfying the signal quality index in the spectrum data set to perform the data interpretation at the first judgment time point, and can also select at least one of the second group of frequency band-light intensity data values satisfying the signal quality index in the spectrum data set to perform the data interpretation at the second judgment time point. The aforesaid method for selecting and interpreting light intensity data values can be applicable between the user and the wearable device, a flow chart of the method can refer to FIG. 4, and the method includes following steps of: controlling the light emitting unit simultaneously emit a mixed light including a plurality of spectrum frequency bands, and the mixed light enter inside skin of the user through a sensing surface (step 41); controlling the spectrum sensing unit sense an intensity of an outgoing light from inside skin of the user at a series of sampling time to generate a spectrum data set (step 42), wherein the spectrum data set includes a plurality of light intensity data values, the plurality of light intensity data values can be divided into a plurality of groups of frequency band-light intensity data values respectively obtained corresponding to the plurality of spectrum frequency bands, and can be respectively divided into a plurality of sampling time-light intensity data value sets corresponding to the series of sampling time; then, according to a signal quality of the plurality of groups of frequency band-light intensity data in the spectrum data set, selecting at least one first group of frequency band-light intensity data values satisfying a signal quality index in the spectrum data set to perform a data interpretation at a first judgment time point (step 43), and selecting at least one second group of frequency band-light intensity data values satisfying the signal quality index in the spectrum data set to perform the data interpretation at a second judgment time point (step 44).

For example, the arithmetic unit 22 can use signal-to-noise ratio (SNR) in the signal quality to select at least a spectrum frequency band-intensity signal curve from the p spectrum frequency band-intensity signal curves corresponding to the p spectrum frequency bands to perform the PPG data interpretation. As for the above application example, in any one of the spectrum frequency band-intensity signal curves, signal components within the frequency band range from a lower limit frequency to an upper limit frequency are defined as the signal, and signal components outside the frequency band range from the lower limit frequency to the upper limit frequency are defined as the noise. For example, if the spectrum frequency band-intensity signal curve represents the signals of blood vessel pulse, the signal component within the frequency range 0.5 Hz~7 Hz can be defined as the signal, and the signal component outside the frequency range 0.5 Hz~7 Hz can be defined as the noise, so the signal-to-noise ratio (SNR) can be respectively calculated for each one of the p spectrum frequency band-intensity signal curves, then at least one of the spectrum frequency band-intensity signal curves of the signal-to-noise ratio greater than a preset value is selected and determined as a qualified spectrum frequency band-intensity signal curve, and the data interpretation (e.g. the PPG data interpretation) is performed to one or more of the qualified spectrum frequency band-intensity signal curve. Another embodiment is to perform a maximum ratio combining (MRC) of the plurality of frequency band-intensity signal curves which meet a signal-to-noise ratio standard according to the signal-to-noise ratio for weighting and combining them into an optimized intensity signal curve, and then to use the optimized intensity signal curve to perform the data interpretation subsequently. The aforesaid PPG data interpretation to the blood vessel changes in the skin of the present application has more information to perform training and judging, so it can also be widely applicable to estimate one value of white blood cell count, red blood cell count, hemoglobin, hematocrit, blood glucose, blood pressure, blood urea nitrogen, creatinine and alanine aminotransferase (ALT) of the user.

The data interpretation of the arithmetic unit 22 performing to the qualified spectrum frequency-intensity signal curves or the optimized intensity signal curves can be the widely used PPG data interpretation, and a data interpretation which is continuously optimized by using artificial intelligence learning (AI learning) and has various cardiovascular status-related data applied thereto. An artificial neural network (ANN) is a mathematical model that imitates structures and functions of human brain and is mainly used to process problems such as regression and classification, with increasing of computing speed and performance of hardware devices such as graphic cards, number of layers of the neutral network model can be greatly deepened, so a number of neuron features that can be trained can also increase accordingly, and thus the neural network model has opportunities to obtain better learning outcomes. However, in the medical field, each information is not easily collected, and amount of the training data is an important key to determining the quality of the model. Therefore, the wearable device completed by the technical means of the present application can simultaneously generate the p spectrum frequency band-intensity signal curves corresponding to the p spectrum frequency bands, more data for training of the artificial intelligence program can be provided in a short time, and accuracy of the data interpretation will be quickly improved.

More preferably, the present application can be optimized by using a transfer learning method. The transfer learning method belongs to a special research field in machine learning, its research source is based on a point of view: when human beings encounter new problems, if they have encountered similar or identical problems in the past, they can more quickly and efficiently solve the new problems based on the experience and knowledge they have learned; that is a process of transferring knowledge. Therefore, as long as a model same as or with tasks related to the neural network model desired to be trained can be found, the model can be used as a source domain model and to train the target domain model through the transfer learning, it is no need to collect data, label data and train model for the target domain from scratch, and the time of collecting data is greatly saved. Therefore, If the amount of data collected by using the micro-spectrometer of the present application is still insufficient, and the results of direct training of the neural network model are usually still unsatisfactory, the present application can use data of MMIC open database (same as "Y. Kurylyak, F. Lamonaca and D. Grimaldi, "A neural network-based method for continuous blood pressure estimation from a PPG signal," in proc. of 2013 IEEE I2MTC, Minneapolis, MN, pp. 280-283, 2013. ") through the transfer learning method as the training data for a source domain neural network model.

Additionally, through observation of the intensity signal curves 310, 320, 330 that change with time and correspond to the plurality of spectrum frequency bands shown in FIG. 3*c*, three-dimensional PPG intensity distribution signals can be seen, if the intensity (height) is converted into a color value, the three-dimensional image can be converted into a flat color image, and the flat color image can be interpreted by using powerful AI image recognition technologies such as convolutional neural network (CNN). Similarly, after the light intensity data values in the spectrum data set were converted into color values, the spectrum data set can also be converted into a flat color image to perform the aforesaid data interpretation.

Furthermore, the arithmetic unit 22 of the present application can determines whether the measuring environment or device wearing conditions are correct according to the p light intensity data values (hereafter snapshot spectrum) corresponding to the p spectrum frequency bands (F1, F2, . . . ,Fp) obtained at a certain sampling time point, can also determine measuring object characteristics (such as race) according to the current snapshot spectrum for selecting the appropriate artificial intelligence models and prediction models. Of course, a measuring parameter can also be selected according to the measuring object characteristics (such as race) determined by the current snapshot spectrum, the various measuring parameters can be, for example, a light source intensity of individual frequency band, sampling speed and measuring times of the spectrum sensing unit 211, even adjustment of lens aperture value for control exposure value. These means are all intended to make the measuring results closer to real state and reduce the chance of misjudgment.

About examples of the signal quality, in addition to determine the signal quality with the direct and convenient signal-to-noise ratio (SNR), an empirical rule can also be used to select, the empirical rule is to compare waveforms with past waveforms and to eliminate it that is too different, or to compare the intensity signal curve of a certain frequency band with the intensity signal curve of a frequency band adjacent thereto, and to eliminate it that is too different. Furthermore, a hindsight determining method can also be used, for example, if the heart rate value, the blood oxygen value or any blood indicator currently predicted after the data interpretation using the intensity signal curve of a certain frequency band is abnormal, significantly beyond possible range value of human beings, the intensity curve of the frequency band can be eliminated, and the intensity signal curves of the remaining frequency bands can be instead used to perform the data interpretation; by repeating such process, the best frequency band signal can be iteratively selected.

In addition to use the mixed light of multiple frequency bands to irradiate the skin to different depths thereof, the light emitting unit 210 of the present application can also be controlled to emit the incident light of the same frequency but different intensities at different time periods (for example, in a time-division multiplexing mode, the incident light of different intensities are emitted in different time slots; certainly, the incident light of different frequency bands and different intensities can also be used. Then, the incident light of different intensities can enter inside skin of the user to different depths through the sensing surface 2000. The spectrum sensing unit 211 can be used to sense an intensity of an outgoing light from inside skin of the user at a series of sampling time to generate a spectrum data set, the spectrum data set includes a plurality of light intensity data values, the plurality of light intensity data values can be divided into a plurality of groups of depth-light intensity data values respectively obtained corresponding to the plurality of incident light intensities. In this way, according to a signal quality of the plurality of groups of depth-light intensity data in the spectrum data set, the arithmetic unit of the present application can select at least one first group of depth-light intensity data values satisfying a signal quality index in the spectrum data set to perform a data interpretation at a first judgment time point, and select at least one second group of depth-light intensity data values satisfying the signal quality index in the spectrum data set to perform the data interpretation at a second judgment time point. In this way, even if the relative displacement occurred between the wearable device and the user due to weak wearing causes variation in arrival depth of the incident light, at least a group of frequency band-light intensity data values measured with the best depth at that time can be instantly select to perform the data interpretation according to the signal quality, so that the misjudgments caused by depth variations can be avoided.

Figure 5:
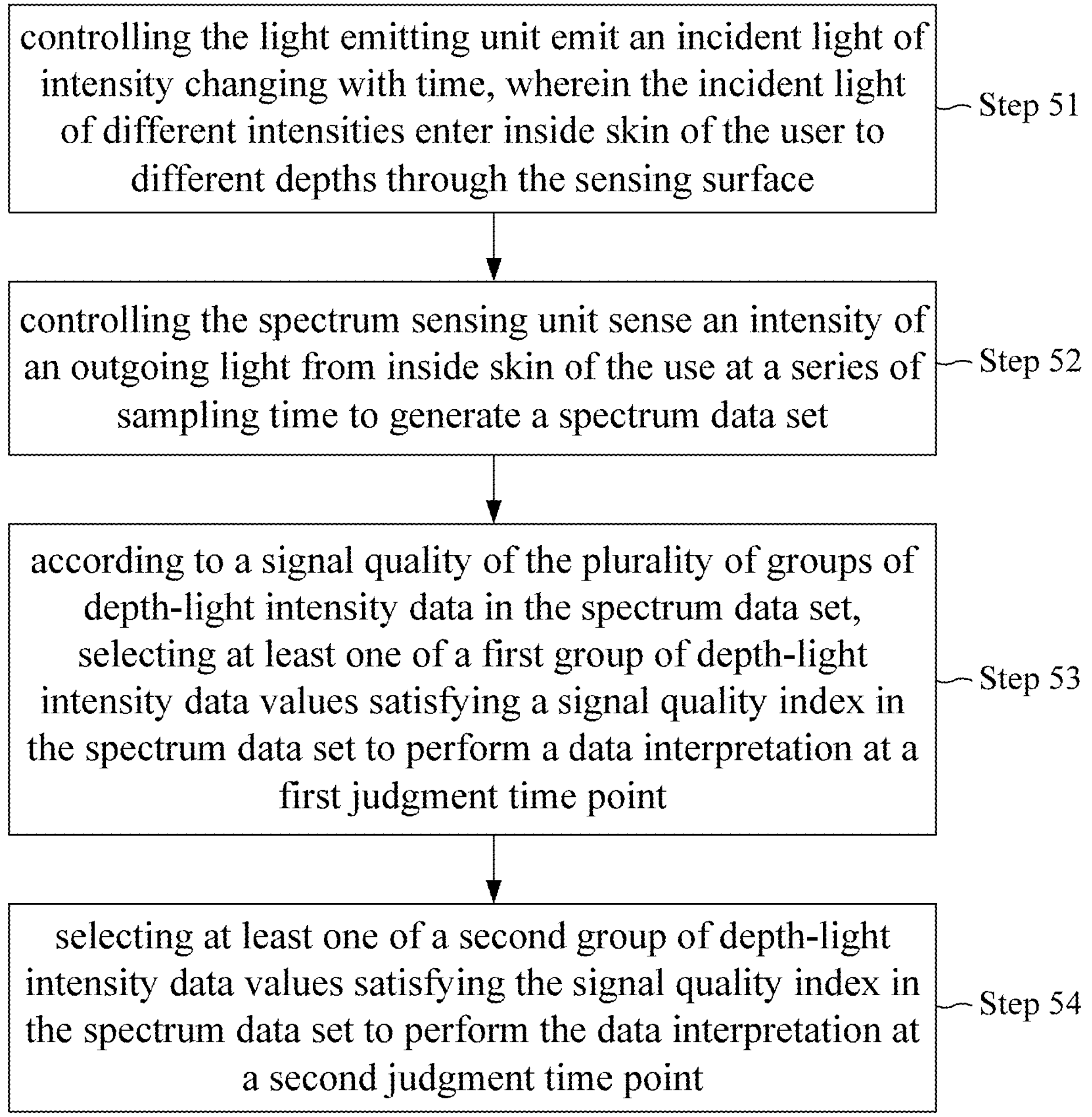
FIG. 5 is a flow chart illustrating another preferred embodiment of the method for selecting and interpreting light intensity data values developed by the present application.

The aforesaid method for selecting and interpreting light intensity data values can be applicable between the user and the wearable device, a flow chart of the method can refer to FIG. 5, and the method includes following steps of: controlling the light emitting unit emit an incident light of intensity changing with time, wherein the incident light of different intensities enter inside skin of the user to different depths through the sensing surface (step 51); controlling the spectrum sensing unit sense an intensity of an outgoing light from the user's skin at a series of sampling time to generate a spectrum data set (step 52), wherein the spectrum data set includes a plurality of light intensity data values, the plurality of light intensity data values can be divided into a plurality of groups of depth-light intensity data values respectively obtained corresponding to the plurality of incident light intensities; then, according to a signal quality of the plurality of groups of depth-light intensity data in the spectrum data set, selecting at least one first group of depth-light intensity data values satisfying a signal quality index in the spectrum data set to perform a data interpretation at a first judgment time point (step 53), and selecting at least one second group of depth-light intensity data values satisfying the signal quality index in the spectrum data set to perform the data interpretation at a second judgment time point (step 54).

In summary, the technology of the present application can improve distortion of the measuring results of the wearable device caused by changes of the incident distance due to displacement between it and the skin, and generate a rich amount of sensing information by using the outgoing light of multiple frequency bands or light intensities to select the better signal, so as to improve the shortcoming of being prone to misjudgment of the traditional wearable device, and to achieve the effects of real-time and effective monitoring of the user' health status. Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A wearable device, applicable to a user, comprising:

a main body, comprising a casing, which comprises a sensing surface configured to be close to skin of the user;

a physiological data sensing module, disposed in the casing, comprising a light emitting unit and a spectrum sensing unit, wherein the light emitting unit is configured to emit a mixed light comprising multiple spectrum frequency bands, and the multiple spectrum frequency bands of the mixed light are configured to simultaneously enter the skin of the user through the sensing surface into different depths inside the skin; the spectrum sensing unit is configured to automatically sense an outgoing light generated from the different depths inside the skin of the user in response to the mixed light at each of a series of sampling time points, thereby obtaining multiple groups of frequency band-light intensity data values of the outgoing light respectively corresponding to the multiple spectrum frequency bands of the mixed light; and an arithmetic unit, in signal communication with the physiological data sensing module, configured to automatically compare a specified parameter of each of the multiple groups of frequency band-light intensity data values received from the physiological data sensing module with a specified index at each of a series of judgement time points, thereby determining respective signal qualities of the multiple groups of frequency band-light intensity data values, wherein at least one of the multiple groups of frequency band-light intensity data values is automatically retrieved for data interpretation by the arithmetic unit based on the respective signal qualities of the multiple groups of frequency band-light intensity data values at each of the series of judgement time points.

2. The wearable device according to claim 1, wherein the sensing surface is configured to be against the skin of a wrist of the user, the physiological data sensing module is a micro spectrometer comprising the light emitting unit and the spectrum sensing unit, the light emitting unit in the micro spectrometer comprises multiple light emitting diodes simultaneously emitting respective light with the multiple spectrum frequency bands to form the mixed light, the spectrum sensing unit in the micro spectrometer senses the outgoing light at each of the series of sampling time points to generate multiple spectrum frequency bands-intensity signal curves corresponding to the multiple groups of the frequency band-light intensity data values, respectively.

3. The wearable device according to claim 2, wherein the arithmetic unit determines the respective signal qualities of the multiple groups of frequency band-light intensity data values by comparing respective signal-to-noise ratio (SNR) values of the multiple spectrum frequency band-intensity signal curves with an SNR threshold.

4. The wearable device according to claim 3, wherein the arithmetic unit is configured to perform a photoplethysmography (PPG) data interpretation according to all of the groups of frequency band-light intensity data values automatically retrieved by the arithmetic unit at the series of judgement time points.

5. The wearable device according to claim 4, wherein the arithmetic unit is configured to automatically generate a white blood cell count, red blood cell count, hemoglobin, hematocrit, blood glucose, blood pressure, blood urea nitrogen, creatinine and/or alanine aminotransferase (ALT) of the user as a result of the PPG data interpretation.

6. The wearable device according to claim 4, wherein the arithmetic unit is configured to optimize the PPG data interpretation by using artificial intelligence learning.

7. The wearable device according to claim 4, wherein the SNR values are configured to include a signal part defined in a range from a lower limit frequency of 0.5 Hz to an upper limit frequency limit of 7 Hz, and a noise part beyond the range, and the arithmetic unit performs a maximum ratio combining of all of the retrieved groups of frequency band-light intensity data values at the series of judgement time points for weighting and combining, thereby obtaining an optimized intensity signal curve for the PPG data interpretation subsequently.

8. The wearable device according to claim 7, wherein the arithmetic unit is configured to automatically generate a white blood cell count, red blood cell count, hemoglobin, hematocrit, blood glucose, blood pressure, blood urea nitrogen, creatinine and/or alanine aminotransferase (ALT) of the user as a result of the PPG data interpretation.

9. The wearable device according to claim 7, wherein the arithmetic unit is configured to optimize the PPG data interpretation by using artificial intelligence learning.

10. The wearable device according to claim 1, wherein the arithmetic unit is configured to convert the retrieved groups of frequency band-light intensity data values at the series of the judgement time points into a color image, which is presented with two-dimensional coordinates sampling time and spectrum frequency band, wherein a color value of a point in the color image corresponds to a light intensity value, and the arithmetic unit is configured to perform the data interpretation on the color image by using an image recognition technology of convolutional neural network.

11. A wearable device, applicable to a user, comprising:

a main body, comprising a casing, which comprises a sensing surface configured to be close to skin of the user;

a physiological data sensing module, disposed in the casing, comprising a light emitting unit and a spectrum sensing unit, wherein the light emitting unit is configured to emit an incident light whose intensity is changing with time, and different intensities of the incident light are configured to sequentially enter the skin of the user and reach different depths under the sensing surface; the spectrum sensing unit is configured to automatically sense an outgoing light generated from one of the different depths inside the skin of the user at each of a series of sampling time points in response to a one of the different intensities of the incident light, thereby obtaining multiple groups of depth-light intensity data values of the outgoing signal corresponding to the one of the different intensities of the incident light; and an arithmetic unit, in signal communication with the physiological data sensing module, configured to automatically compare a specified parameter of each of the multiple groups of depth-light intensity data values received from the physiological data sensing module with a specified index at each of a series of judgement time points, thereby determining respective signal qualities of the multiple groups of depth-light intensity data values, wherein at least one of the multiple groups of depth-light intensity data values is automatically retrieved for data interpretation by the arithmetic unit based on the respective signal qualities of the multiple groups of depth-light intensity data values at each of the series of judgement time points.

12. A method for physiological data interpretation of a wearable device, wherein the wearable device comprises a sensing surface configured to be close to skin of a user, and a light emitting unit and a spectrum sensing unit configured to obtain physiological data of the user through the skin, the method comprising:

the light emitting unit emitting a mixed light comprising multiple spectrum frequency bands when the wearable device is activated for the physiological data interpretation, wherein the multiple spectrum frequency bands of the mixed light are configured to simultaneously enter the skin of the user through the sensing surface into different depths inside the skin;

the spectrum sensing unit automatically sensing an outgoing light generated from the different depths inside the skin of the user at each of a series of sampling time points, thereby obtaining multiple groups of frequency band-light intensity data values of the output signal respectively corresponding to the multiple spectrum frequency bands of the mixed light;

automatically comparing a specified parameter of each of the multiple groups of frequency band-light intensity data values with a specified index at each of a series of judgement time points, thereby determining respective signal qualities of the multiple groups of frequency band-light intensity data values, wherein at least one of the multiple groups of frequency band-light intensity data values is automatically retrieved based on the respective signal qualities of the multiple groups of frequency band-light intensity data values at each of the series of judgement time points; and performing the physiological data interpretation according to the retrieved groups of frequency band-light intensity data values at the series of judgement time points.

13. A method for physiological data interpretation of a wearable device, wherein the wearable device comprises a sensing surface configured to be close to skin of a user, and a light emitting unit and a spectrum sensing unit configured to obtain physiological data of the user through the skin, the method comprising:

the light emitting unit emitting an incident light whose intensity is changing with time, wherein different intensities of the incident light are configured to sequentially enter the skin of the user and reach different depths under the sensing surface;

the spectrum sensing unit automatically sensing an outgoing light generated from one of the different depths inside the skin of the user at each of a series of sampling time points in response to one of the different intensities of the incident light, thereby obtaining multiple groups of depth-light intensity data values of the outgoing signal corresponding to the one of the different intensities of the incident light; and automatically comparing a specified parameter of each of the multiple groups of depth-light intensity data values with a specified index at each of a series of judgement time points, thereby determining respective signal qualities of the multiple groups of depth-light intensity data values, wherein at least one of the multiple groups of depth-light intensity data values is automatically retrieved based on the respective signal qualities of the multiple groups of depth-light intensity data values at each of the series of judgement time points; and performing the physiological data interpretation according to the retrieved groups of depth-light intensity data values at the series of judgement time points.

* * * * *